United States Patent [19]

Combates et al.

[11] Patent Number: 6,045,998
[45] Date of Patent: *Apr. 4, 2000

[54] TECHNIQUE FOR DIFFERENTIAL DISPLAY

[75] Inventors: Nicholas Combates, New Brunswick, N.J.; Jose R. Pardinas, Staten Island, N.Y.; Satish Parimoo, Bridgewater, N.J.; Stephen M. Prouty, Doylestown, Pa.; Kurt S. Stenn, Princeton, N.J.

[73] Assignee: Johnson & Johnson Consumer Products, Inc., Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/832,021

[22] Filed: Apr. 2, 1997

Related U.S. Application Data

[60] Provisional application No. 60/014,666, Apr. 3, 1996.

[51] Int. Cl.[7] ............................... C12Q 1/68; C12P 19/34
[52] U.S. Cl. .................................. 435/6; 435/91.2
[58] Field of Search ................ 435/6, 7.5, 91.2; 436/94; 536/23.1, 24.3, 24.33; 935/17, 18, 19, 77

[56] References Cited

U.S. PATENT DOCUMENTS

| | | | |
|---|---|---|---|
| 5,599,672 | 2/1997 | Liang et al. | 435/6 |
| 5,665,547 | 9/1997 | Pardee et al. | 435/6 |

FOREIGN PATENT DOCUMENTS

| | | |
|---|---|---|
| 0 372 524 | 6/1989 | European Pat. Off. . |
| 6-303997 | 11/1994 | Japan . |
| 89/12695 | 12/1989 | WIPO . |

OTHER PUBLICATIONS

Liang and Pardee. Differential Display of Eukaryotic Messenger RNA by Means of the Polymerase Chain Reaction. Science 257: 967–971, Aug. 1992.

Liang et al. Analysis of Altered Gene Expression by Differential Display. Methods Enzymol. 254: 304–321, 1995.

Liang et al. Recent Advances in Differential Display. Curr. Opinion Immunol. 7: 274–280, 1995.

JPO Abstract No. JP406303997A, "Determination of cDNA", Takagi et al, Nov. 1, 1994.

Ace C.I., Balsamo M., Le L.T., Okulicz W.C. (1994) Isolation of Progesterone–Dependent Complementary Deoxyribonucleic Acid Fragments from Rhesus Monkey Endometrium by Sequential Subtractive Hybridization and Polymerase Chain Reaction Amplification. Endocrinology. vol.134, No. 3: 1305–1309.

Ayala M., Balint R.F., Fernandez–de–Cossio M.E., Canaan–Haden L., Larrick J.W., Gavilondo J.V. (1995) New Primer Strategy Improves Precision of Differential Display. Biotechniques. vol. 18, No. 5: 842–849.

*Primary Examiner*—David Guzo
*Assistant Examiner*—Thomas G. Larson

[57] ABSTRACT

The method of this invention relates to the use of improved anchor primers and a novel purification process to increase the efficiency and accuracy of the differential display technique.

13 Claims, 12 Drawing Sheets

FIG. 2
TITRATION OF
cDNA INPUT
A. T12GG
1. 200 pg
2. 160
3. 100
4. 50
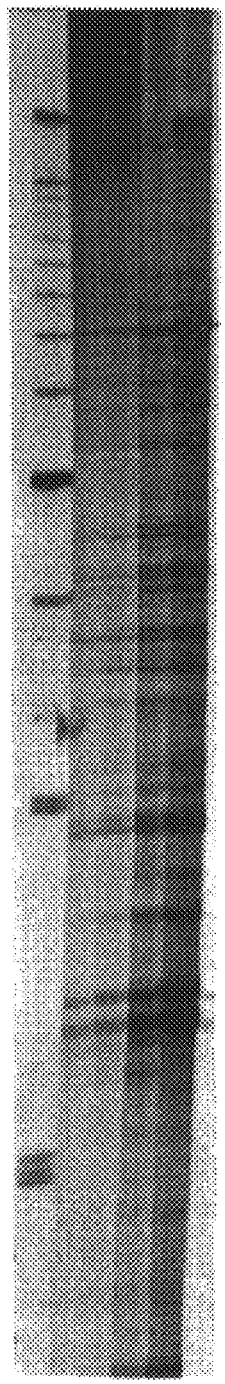
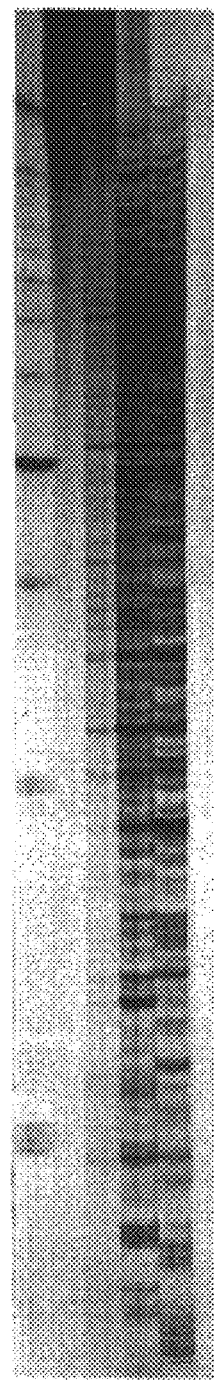
B. T12CA
1. 25.0 pg
2. 10.0
3. 5.0
4. 2.5

FIG. 4A

Anchor Primers used by Liang and Pardee

TTTTTTTTTTTAA   TTTTTTTTTTTCA
TTTTTTTTTTTAC   TTTTTTTTTTTCC
TTTTTTTTTTTAG   TTTTTTTTTTTCG
TTTTTTTTTTTAT   TTTTTTTTTTTCT

TTTTTTTTTTTGA
TTTTTTTTTTTGC
TTTTTTTTTTTGG
TTTTTTTTTTTGT

FIG. 4B

Enhanced Specificity Anchor Primers used in the Invention

TTTTTTTTTAAA   TTTTTTTTTACA   TTTTTTTTTAGA   TTTTTTTTTATA
TTTTTTTTTAAC   TTTTTTTTTACC   TTTTTTTTTAGC   TTTTTTTTTATC
TTTTTTTTTAAG   TTTTTTTTTACG   TTTTTTTTTAGG   TTTTTTTTTATG
TTTTTTTTTAAT   TTTTTTTTTACT   TTTTTTTTTAGT   TTTTTTTTTATT

TTTTTTTTTCAA   TTTTTTTTTCCA   TTTTTTTTTCGA   TTTTTTTTTCTA
TTTTTTTTTCAC   TTTTTTTTTCCC   TTTTTTTTTCGC   TTTTTTTTTCTC
TTTTTTTTTCAG   TTTTTTTTTCCG   TTTTTTTTTCGG   TTTTTTTTTCTG
TTTTTTTTTCAT   TTTTTTTTTCCT   TTTTTTTTTCGT   TTTTTTTTTCTT

TTTTTTTTTGAA   TTTTTTTTTGCA   TTTTTTTTTGGA   TTTTTTTTTGTA
TTTTTTTTTGAC   TTTTTTTTTGCC   TTTTTTTTTGGC   TTTTTTTTTGTC
TTTTTTTTTGAG   TTTTTTTTTGCG   TTTTTTTTTGGG   TTTTTTTTTGTG
TTTTTTTTTGAT   TTTTTTTTTGCT   TTTTTTTTTGGT   TTTTTTTTTGTT

ENHANCED SPECIFICITY ANCHOR PRIMERS

ENHANCED SPECIFICITY ANCHOR PRIMERS

Subtraction Procedure

SEQUENCE LISTING

<160> NUMBER OF SEQ ID NOS: 64

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: arbitrary
      upstream oligonucleotide

<400> SEQUENCE: 1
aaactccgtc                                                           10

<210> SEQ ID NO 2
<211> LENGTH: 10
<212> TYPE: DNA

```
<213> ORGANISM: Artificial Sequence
<220> FEATURE:
<223> OTHER INFORMATION: Description of Artificial Sequence: arbitrary
      upstream oligonucleotide

<400> SEQUENCE: 2
tcgatacagg                                                              10

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: "n" bases may be A, T, C or G

<400> SEQUENCE: 3
tttttttttt ttnnn                                                        15

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: example
      sequence

<400> SEQUENCE: 4 agcccttta a gcgatgcatg ggcacgaaaa aaaaaaaa                               38

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 5
tttttttttt ttaa                                                         14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 6
tttttttttt ttac                                                         14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 7
tttttttttt ttag                                                         14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 8
tttttttttt ttat                                                      14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 9
tttttttttt ttca                                                      14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 10
tttttttttt ttcc                                                      14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 11
tttttttttt ttcg                                                      14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 12
tttttttttt ttct                                                      14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 13
tttttttttt ttga                                                      14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 14
tttttttttt ttgc                                                      14

<210> SEQ ID NO 15
```

<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 15
tttttttttt ttgg                                              14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 16
tttttttttt ttgt                                              14

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 17
tttttttttt ttaaa                                             15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 18
tttttttttt ttaac                                             15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 19
tttttttttt ttaag                                             15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 20
tttttttttt ttaat                                             15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 21

-continued tttttttttt ttcaa                                                          15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 22
tttttttttt ttcac                                                          15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 23
tttttttttt ttcag                                                          15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 24
tttttttttt ttcat                                                          15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 25
tttttttttt ttgaa                                                          15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 26
tttttttttt ttgac                                                          15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 27
tttttttttt ttgag                                                          15

<210> SEQ ID NO 28
<211> LENGTH: 15
<212> TYPE: DNA

```
<213> ORGANISM: Artificial Sequence
<220> FEATURE:
<223> OTHER INFORMATION: Description of Artificial Sequence: primer

<400> SEQUENCE: 28
tttttttttt ttgat                                                        15

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 29
tttttttttt ttaca                                                        15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 30
tttttttttt ttacc                                                        15

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 31
tttttttttt ttacg                                                        15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
tttttttttt ttact                                                        15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 33
tttttttttt ttcca                                                        15

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 34
tttttttttt ttccc                                                        15
```

```
<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 35
tttttttttt ttccg                                                    15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 36
tttttttttt ttcct                                                    15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 37
tttttttttt ttgca                                                    15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 38
tttttttttt ttgcc                                                    15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 39
tttttttttt ttgcg                                                    15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 40
tttttttttt ttgct                                                    15

<210> SEQ ID NO 41
<211> LENGTH: 15
<212> TYPE: DNA
<213> ORGANISM: Artificial Sequence
<220> FEATURE:
```

<223> OTHER INFORMATION: Description of Artificial Sequence: primer

<400> SEQUENCE: 41
tttttttttt ttaga                                                    15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 42
tttttttttt ttagc                                                    15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 43
tttttttttt ttagg                                                    15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 44
tttttttttt ttagt                                                    15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 45
tttttttttt ttcga                                                    15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 46
tttttttttt ttcgc                                                    15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 47
tttttttttt ttcgg                                                    15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 48
tttttttttt ttcgt                                                    15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 49
tttttttttt ttgga                                                    15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 50
tttttttttt ttggc                                                    15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 51
tttttttttt ttggg                                                    15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 52
tttttttttt ttggt                                                    15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 53
tttttttttt ttata                                                    15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 54
tttttttttt ttatc                                            15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 55
tttttttttt ttatg                                            15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 56
tttttttttt ttatt                                            15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 57
tttttttttt ttcta                                            15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 58
tttttttttt ttctc                                            15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 59
tttttttttt ttctg                                            15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 60
tttttttttt ttctt                                            15

<210> SEQ ID NO 61
<211> LENGTH: 15

```
<212> TYPE: DNA
<213> ORGANISM: Artificial Sequence
<220> FEATURE:
<223> OTHER INFORMATION: Description of Artificial Sequence: primer

<400> SEQUENCE: 61 ttttttttttt ttgta                                               15

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 62 ttttttttttt ttgtc                                               15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 63 ttttttttttt ttgtg                                               15

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 64 ttttttttttt ttgtt                                               15
```

TECHNIQUE FOR DIFFERENTIAL DISPLAY

This Application claims the benefit of provisional application 60/014666 filed on Apr. 3, 1996, which is incorporated herein by reference.

FIELD OF THE INVENTION

This invention relates to improved methods of using the differential display technique to identify genes that are differentially regulated by cells under various physiological or experimental conditions. It also relates to an improved method for extracting purified cDNA by subtraction.

BACKGROUND OF THE INVENTION

Techniques designed to identify genes that are differentially regulated by cells under various physiological or experimental conditions (for example, differentiation, carcinogenesis, pharmacologic treatment) have become pivotal to modern biology. Differential display is one of the latest additions to the repertoire of such techniques. This technique was introduced by Liang and Pardee and described in U.S. Pat. No. 5,262,311. Prior to Liang and Pardee's introduction of this technique, those interested in identifying differentially expressed genes were compelled to resort either to differential hybridization screening (Zimmerman, G. R., et al., Cell, Vol. 21, pp. 709–715 (1980)) or to subtractive hybridization screening (St. John, T. P. et al., Cell, Vol. 16, pp. 443–452 (1979)) of complementary deoxynucleic acid ("cDNA") libraries. Neither of these methods is entirely satisfactory; both are time consuming and labor intensive. Of the two, differential hybridization (also known as ± screening) is particularly insensitive, being essentially confined to the detection of relatively large differences between high to moderate-abundance transcripts. Subtractive hybridization, while far more sensitive than ± screening, is also technically far more demanding. Furthermore, it is necessary to carry out two separate subtractive hybridization experiments in order to identify both up- and down-regulated gene expression.

Differential display offers an attractive alternative to differential and subtractive hybridization screening. Generally, Liang et al. describes a protocol which involves the reverse transcription of a messenger ribonucleic acid ("mRNA") population, in independent reactions, with each of twelve anchor primers ($T_{12}MN$), where M can be G (guanine), A (adenine) or C (cystosine) and N can be G, A, C or T (thymidine). The resulting single-stranded cDNAs are then amplified by the polymerase chain reaction (hereinafter, "PCR") using the same anchor primer used for reverse transcription together with an upstream or 5' decamer of arbitrary sequence. The PCR products, which are labeled by incorporation of tracer amounts of a radioactive nucleotide, are resolved for analysis by denaturing polyacrylamide gel electrophoresis (PAGE). This technique permits the visualization of both up- and down-regulated gene expression simultaneously in the same experiment. Liang et al. postulated that each two-primer combination could amplify only a limited subpopulation of cDNAs, and that the twelve anchor primers together with twenty arbitrary decamers (i.e., 240 PCR reactions) should result in the display of the 3' termini of all distinct mRNAs that are theoretically expressed in any given cell type (Liang, P. and Pardee, A. B., Science, Vol. 257, pp. 967–971 (1992)).

Although a number of laboratories have used Liang et al.'s differential display technique to identify differentially expressed genes, the successful implementation of differential display remains highly elusive for many researchers. Principal difficulties include poor reproducibility and large numbers of false positive results.

For example, more recently, Liang and Pardee obtained U.S. Pat. No. 5,599,672 which describes a method for isolating mRNAs as cDNAs employing a polymerase amplification method using at least two oligodeoxynucleotide primers. In one approach, the first primer contains a sequence capable of hybridizing to a site immediately upstream of the first A ribonucleotide of the mRNA's polyA tail and the second primery contains an arbitrary sequence. In another approach, the first primer contains a sequence capable of hybridizing to a site including the mRNA's poly A signal sequence and the second primer contains an arbitrary sequence. The '672 patent mentions the use of three or more nucleotides that can hybridize to an mRNA sequence that is immediately upstream of the polyA tail, however, it states that using such a first primer is not practical for rapid screening of the mRNAs contained within a given cell line due to the number of oligodeoxynucleotides required to identify every mRNA.

Villeponteau et al., in U.S. Pat. No. 5,580,726 describes a method for detecting and isolating differentially expressed mRNAs using first oligonucleotide primers for reverse transcription of mRNAs and both the first oligonucleotide primers and second oligonucleotide primers for replication of the resultant cDNAs. These primers have a length of at least twenty-one (21) nucleotides. Furthermore, Villeponteau et al. direct their claims towards the cycling parameters of the PCR reaction. Although this method may provide additional information in screening the mRNAs, as suggested by Liang and Pardee, we would expect that it would still result in a possibly significant number of false positives due to the presence of artifacts.

We have found that the problems with the prior techniques are due to several previously unrecognized and unappreciated factors that critically affect the accuracy of differential display techniques. Thus, it is an object of our invention to improve the method of using differential display techniques to identify genes.

It is another object of our invention to improve the method of using differential display techniques to identify genes to obtain better reproducibility of results.

It is yet another object of our invention to improve the method of using differential display techniques to identify genes by increasing the number of true positive results and substantially eliminating false positives.

It is another object of our invention to improve the accuracy of the results obtained by using the differential display method to identify genes.

It is yet another object of our invention to obtain pure cDNA fragments by an improved subtraction method.

SUMMARY OF THE INVENTION

This invention provides an improved method of performing differential display including but not limited to screening differences in gene expression between various cell types or between cell in different stages of development or cells under different pharmacological conditions. The technique is highly reproducible and results in very significantly lower numbers of false positives than those of previously-known techniques. The method of this invention uses the polymerase chain reaction (PCR) to amplify cDNA produced from a selected set of expressed mRNA sequences from particular cell types. The method of this invention has the following steps:

1) reverse transcription of sample mRNAs using an oligo(dT) primer having from about 12 to about 18 T nucleotides to produce cDNA;

2) quantification of the cDNA resulting from reverse transcription of step (1) to determine the amount of cDNA produced;

3) performing a polymerase chain reaction, said performance comprising:

a) titration of the cDNA, by running at least two different concentrations of the cDNA through the PCR; and b) simultaneously with step (a), adding at least one anchor primer having the sequence $T_{12}MNN$, wherein M is A, G or C and N is A, G, C or T;

4) removing cDNA from the resulting gel and reamplifying said cDNA; and 5) subtracting contaminating cDNAs from the reamplified product.

This invention also provides for improving the subtraction method itself which includes the use of biotinylated deoxynucleotides as upstream and/or downstream anchor primers to remove contaminants and recover the purified cDNA product which can then be re-amplified and cloned into a plasmid vector.

BRIEF DESCRIPTION OF THE DRAWINGS

FIGS. 2A and 2B are photographs of a gel depicting the effect of templates cDNA input on the behavior of differential display pattern.

FIG. 4A is a table of parent anchor primers.

FIG. 4B is a table of enhanced-specificity anchor primers.

FIG. 6 is a photograph of gels made using the method of this invention to demonstrate the rescue of non-working anchor primers.

FIG. 7A represents a gel demonstrating a differentially displayed cDNA. FIG. 7B represents a gel showing a reamplified product from FIG. 7A. FIG. 7C represents a gel showing the products of the gels of FIGS. 7A and 7B after subcloning and fingerprinting with enzyme Hinf I.

FIG. 9B is a photograph of gels demonstrating a better resolution when the primers themselves are biotinylated.

FIG. 9C is a photograph of gels demonstrating the products of FIG. 9B after elution and reamplification.

DETAILED DESCRIPTION OF PREFERRED EMBODIMENTS

Figure 1:
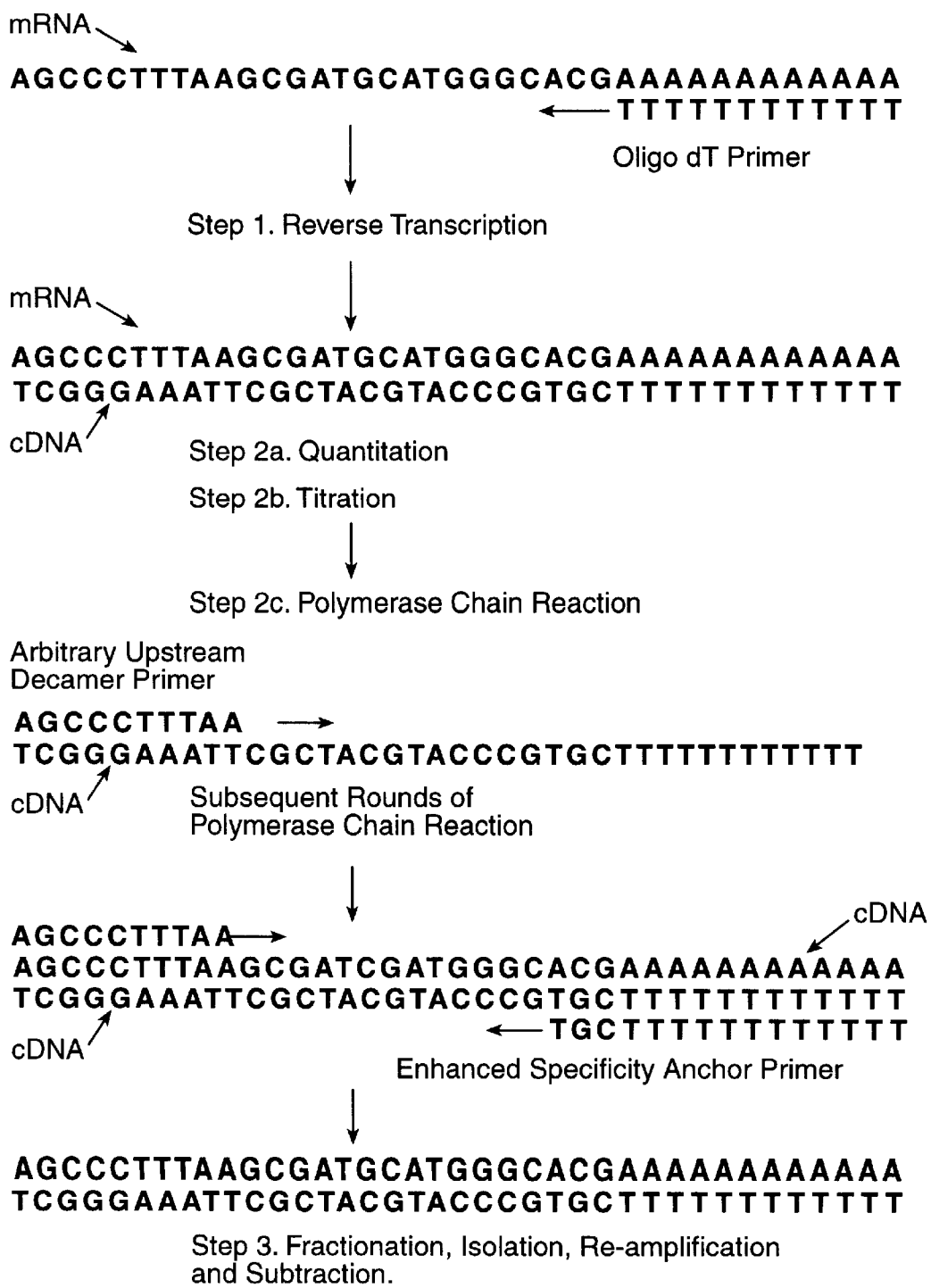
FIG. 1 depicts one embodiment of the differential display method of this invention.

The method of this invention features, in a first aspect, an improved method for detecting differences in gene expression which involves, first, contacting nucleic acid which contains an mRNA sequence with a first oligonucleotide primer, wherein the first oligonucleotide primer has a hybridizing sequence sufficiently complementary to a region of the mRNA to hybridize therewith. One embodiment of the method of this invention is set forth in the diagram of FIG. 1. Referring to FIG. 1, step 1 of the method of this invention is a reverse transcription of mRNA into complementary DNA. The method of the invention uses an oligo dT primer to react with mRNA. The oligo dT primer is reacted with two or more mRNA samples for later comparison. Advantageously, this primer should comprise an oligo(dT)$_{12\text{-}18}$ primer rather than a so-called "anchor" primer, as used in previously-known methods. The Liang and Pardee method for example, used anchor primers in the initial reverse transcription step. The anchor primers, having a sequence of $T_{12}MN$, where M is A, C, or G and N is A, C, G or T, produced twelve separate cDNA populations. This olig(dT)$_{12\text{-}18}$ primer hybridizes to the poly A tail of the mRNA, which is present on all mRNA, except for a small minority of mRNA. The use of the oligo dT primer results in only one reaction and produces only one cDNA population. This greatly increases the efficiency of the method by generating a substantially standard pool of single-stranded cDNA from each experimental mRNA population. Such standard pools of cDNA are easily quantitated by spectrophotometry and their inputs into the PCR amplification step can be precisely controlled in accordance with techniques well-known to those of ordinary skill in the art.

The oligonucleotide (oligo dT) primer is therefore contacted with the mRNA to produce a first complementary DNA ("cDNA") primer product. Preferably, the cDNA produced at this point in the method is measured to determine the quantity of cDNA produced. Preferably, this determination is made using ultraviolet spectroscopy, although any standard procedure known for quantifying cDNA known to those of ordinary skill in the art is acceptable for use for this purpose. When using the UV spectroscopy procedure, an absorbance of about 260 nm of UV light should be used.

As set forth in FIG. 1, the cDNA produced in the initial hybridization reaction should then be titrated into the PCR process by running several PCR reactions at decreasing concentrations of cDNA. This step in the method of this invention quantifies and contributes to optimizing the concentration of cDNA which should be used in the remaining steps of the method. Essentially, this serves to calibrate the method and protect the method against false positive results. We theorize that, at higher concentrations of cDNA used in the PCR process, the cDNA tends to produce higher molecular weight products. At lower concentrations, the PCR process tends to obtain lower molecular weight species that do not appear at higher cDNA concentrations. In previous methods, a fixed volume of cDNA solution was added to the remaining steps, without determination of the actual amount of cDNA present in the solution used. Without a calibration or titration of the cDNA concentrations, the cDNA quantity was unknown and not standardized between or among samples. Thus, certain bands may have appeared on one resulting PCR gel which may not have appeared in a comparative sample. Previously, there would be no method by which to determine whether this difference in the samples was due to cDNA concentration or to an actual positive result which indicated the presence of species in one sample and not the other.

There appears to be a fairly narrow range of cDNA concentrations (from about 250 to about 10 pg) over which a crisp, well-populated, reproducible display may be generated. The range may be subdivided into from about four to about ten concentrations which are to be subjected to polymerase chain reaction. The polymerase chain reaction may be performed in the presence of traditional anchor primers (i.e., $T_{12}MN$) or the enhanced specificity primers of this invention. Notably, the calibration performed using the traditional anchor primers is applicable to the enhanced specificity primers of this invention which are derived from those parent traditional anchor primers. Concentrations of cDNA above this range result in: (1) the accumulation of high molecular weight products which cannot be resolved by gel electrophoresis under denaturing conditions; and/or (2) a reduction in the number and intensity of cDNAs. Notably, different primers and primer combinations behave similarly at different (primer-specific) cDNA concentrations. Thus, a calibration is preferably conducted for each primer used in the method of this invention. Reducing the cDNA input to values below the optimal range results in a gradual decline in the number of cDNAs as well as in increasingly erratic display patterns as shown in FIG. 2. A demonstration of the high reproducibility that can be achieved at cDNA concentrations within the optimal range is shown in FIG. 3.

For example, FIG. 2 depicts the gels which result with decreasing amounts of cDNA inputs. FIG. 2 demonstrates that as the cDNA input quantity decreases, the differential display reaction becomes better resolved. In FIG. 2A, the PCR products were generated using only anchor primers $T_{12}GG$. Lane M depicts the track of the molecular weight marker; Lane 1, 200 pg cDNA; Lane 2, 160 pg cDNA; Lane 3, 100 pg cDNA; and Lane 4, 50 pg cDNA. In FIG. 2B, the PCR products were generated using only anchor primer $T_{12}CA$. Lane M depicts the track of the molecular weight marker; Lane 1, 25 pg cDNA; Lane 2, 10 pg cDNA; Lane 3, 5 pg cDNA; and Lane 4, 2.5 pg cDNA. As shown in FIG. 2B, Lane 4, many additional bands representing additional species are apparent at the lower cDNA concentrations.

Figure 3:
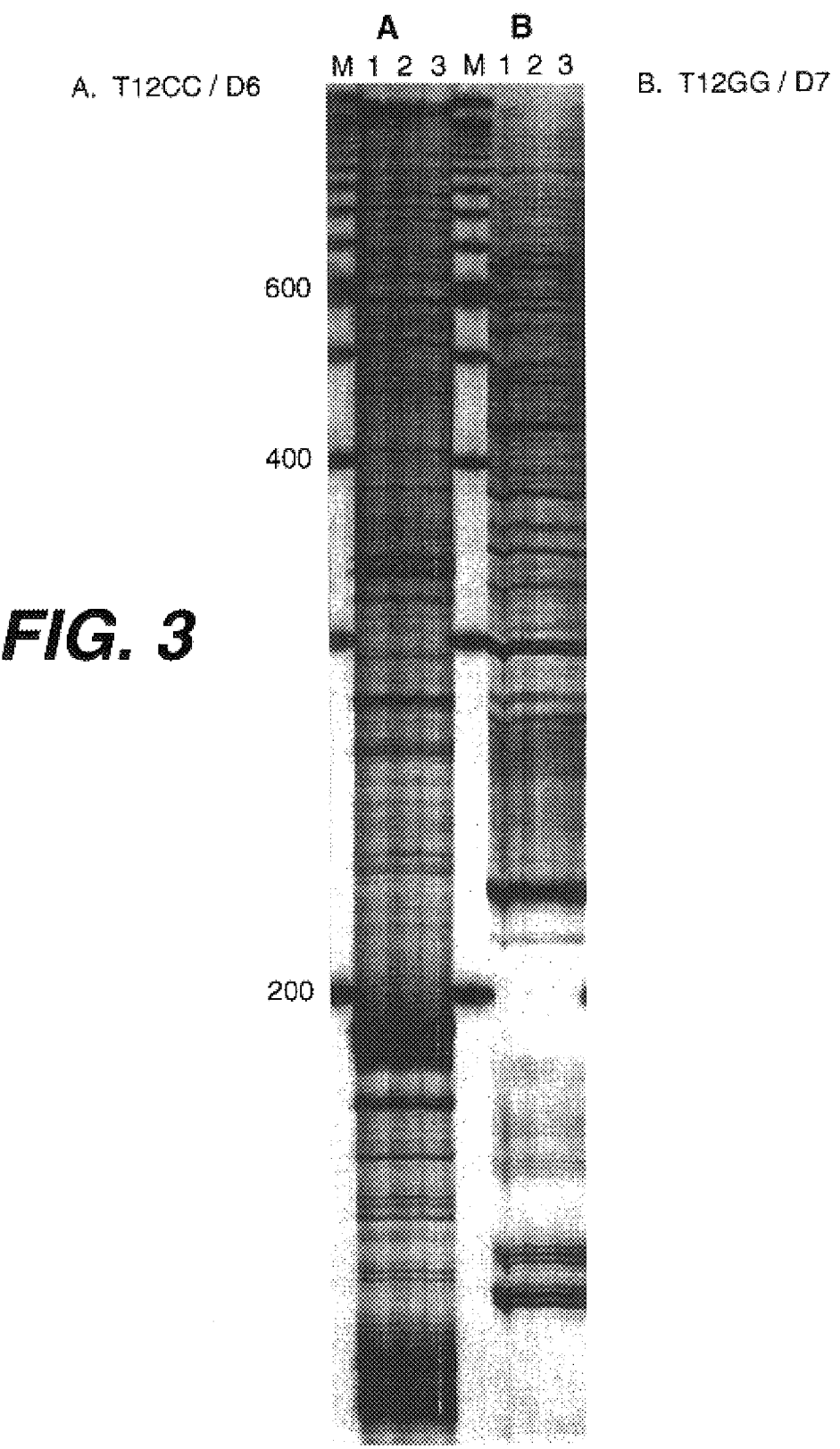
FIGS. 3A and 3B are photographs of gels produced using the method of the invention, depending the high reproducibility of the differential display reaction method of this invention with the optimum range of template cDNA input.

The use of cDNA concentrations within the optimal range for each primer results in highly reproducible data, as set forth in FIG. 3. FIG. 3A demonstrates the reproducibility of results using anchor primer $T_{12}CC$ and arbitrary oligonucleotide D6, 5'AAACTCCGTC3'. Lane M represents the molecular weight marker; Lanes 1–3, cDNA input of 100 pg. FIG. 3B depicts triplicate reactions using anchor primer $T_{12}GG$ and arbitrary oligonucleotide D7 5'TCGATACAGG3'. Lane M represents molecular weight marker; Lanes 1–3, cDNA input of 100 pg.

Preferably, in order to increase the specificity and accuracy of the method of this invention, the PCR amplification includes the use of a 3' oligonucleotide primer having at least three nucleotides which can hybridize to a sequence which is immediately 5' to the poly A tail, $T_{12}MNN$, wherein M is A, G or C and N is A, G, C or T Appropriate preferable primers are illustrated in FIG. 4B. Of course, the more nucleotides used, the more accurate the method. However, depending upon the time available for analysis, it is more desirable to use the least number of base pairs possible without sacrificing an inordinate amount of accuracy. We have found three nucleotides in addition to the thymidine chain to be most preferable, although between about three to about five may be used and up to seven are possible for use in the method.

In the original differential display method outlined by Liang and Pardee in 1992, only twelve anchor primers of type $T_{12}MN$ were introduced. Examples of these anchor primers are listed in FIG. 4A. This class of anchor primers is enlarged using the method of this invention by retaining the oligo(dT)$_{12}$ tail while extending by one the number of nucleotides at the 3', or specificity end, of the molecule, as shown in FIG. 4B. The resulting enhanced-specificity anchor primers constitute a family with the general structure $T_{12}MNN$, where M and N retain their original meaning. In essence, from each of the traditional "parent" anchor primers, four enhanced-specificity anchor primers can be generated (e.g. $T_{12}CCA$, $T_{12}CCC$, $T_{12}CCG$, and $T_{12}CCT$ can be derived from $T_{12}CC$). Of course, additional nucleotides in excess of three may be added in order to increase the specificity of the reaction. However, if too many are added, the efficiency of the method is greatly reduced, as the number of reaction products increases as the number of nucleotides increases. Thus, it is preferable to use between three and seven nucleotides in addition to the T-tail; more preferable to use between three and five and most preferable to use three.

Figure 5:
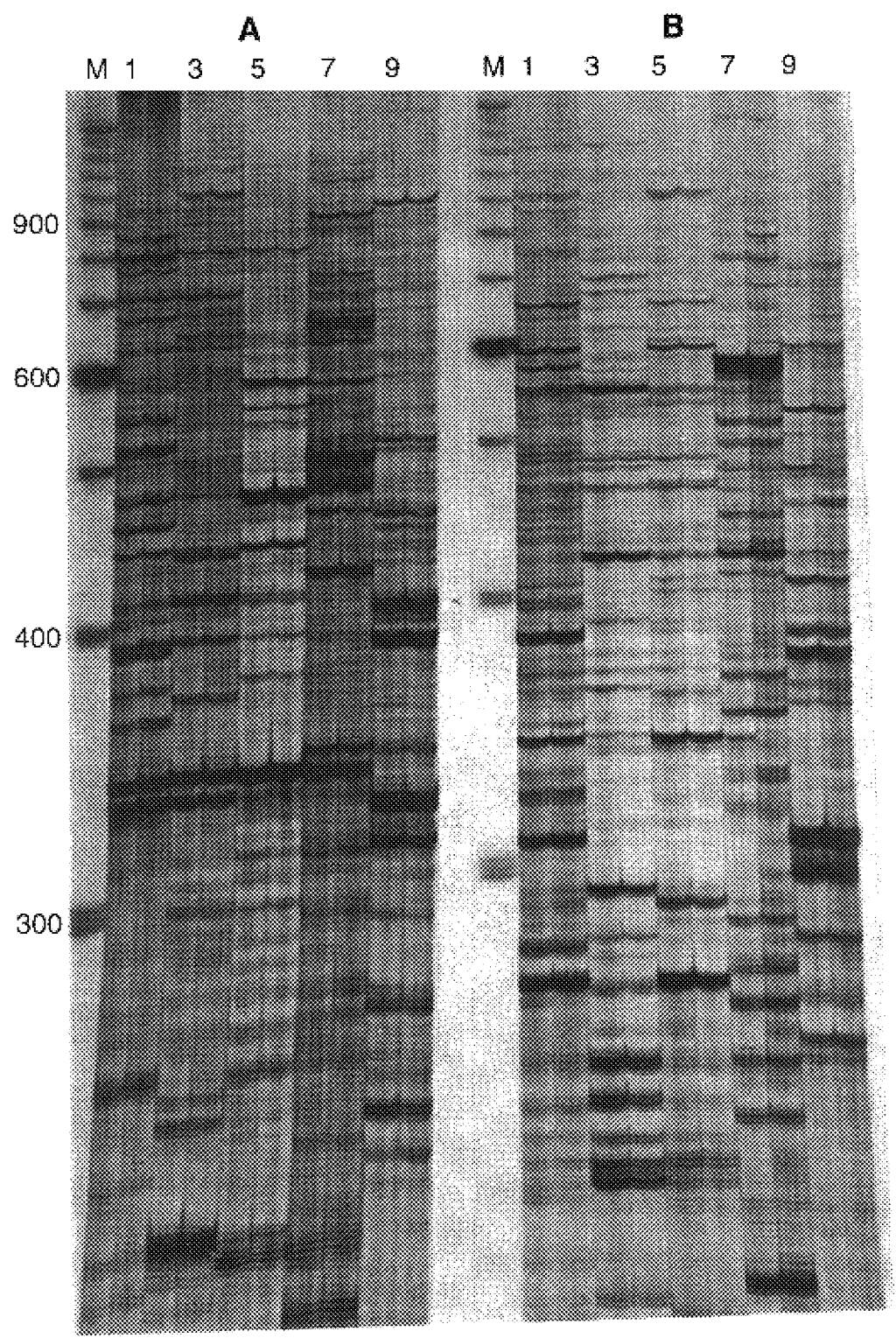
FIGS. 5A and 5B are photographs of gels made using the method of the invention. It depicts the effect of the enhanced-specificity anchor primers on the differential display result.
Figure 5:
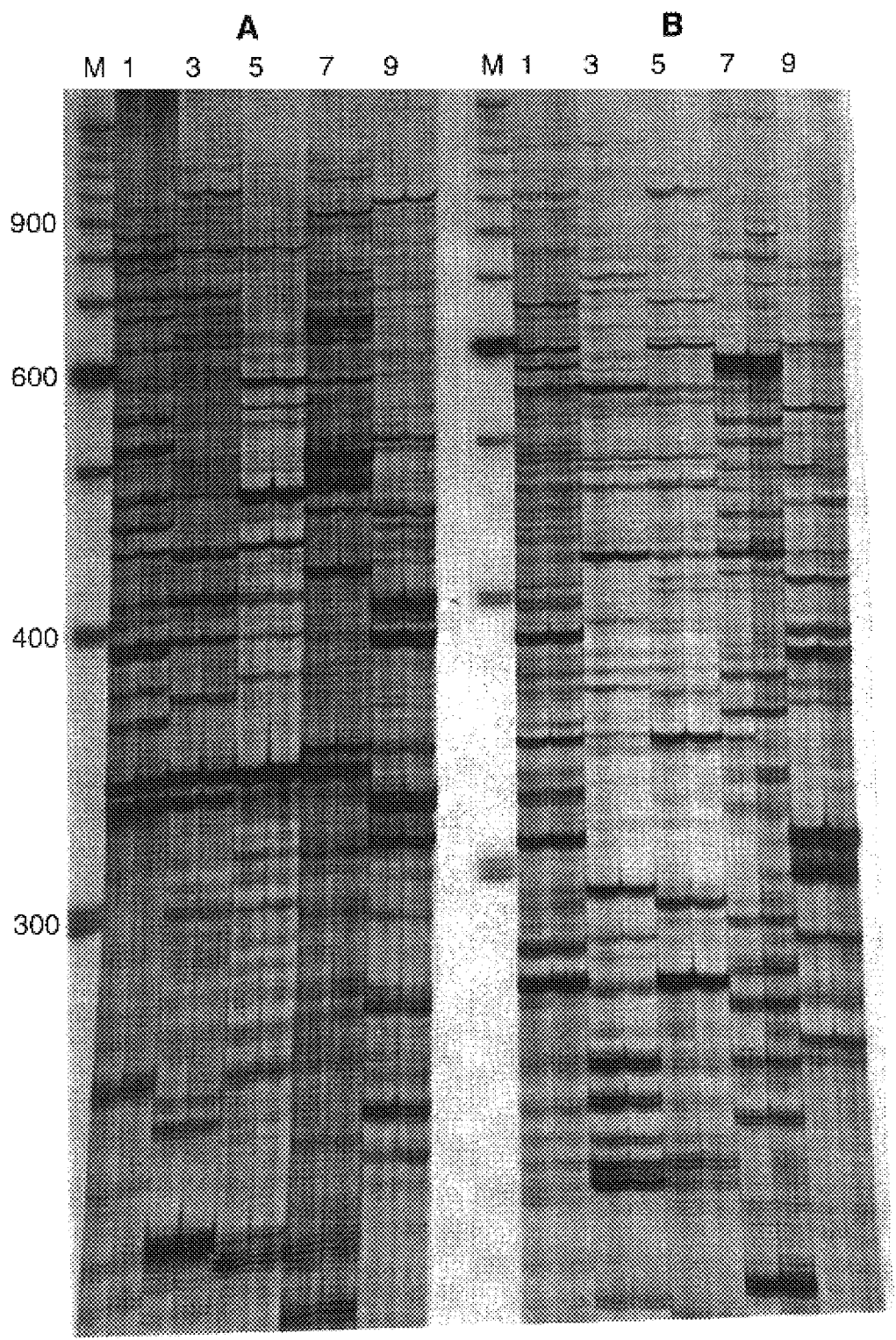

Side-by-side comparisons between the parent anchor primer and the four derived enhanced-specificity anchor primers are demonstrated in FIGS. 5A and 5B. In FIG. 5A the molecular weight marker is in Lane M and the display pattern generated by the traditional parent anchor primer $T_{12}CC$ is in lanes 1 and 2. The enhanced-specificity anchor primers, $T_{12}CCA$ in lanes 3 and 4, $T_{12}CCC$ in lanes 5 and 6, $T_{12}CCG$ in lanes 7 and 8, and $T_{12}CCT$ in lanes 9 and 10 are shown. In FIG. 5B the molecular weight marker is in Lane M and the display pattern generated by the traditional parent $T_{12}GG$ anchor is in lanes 1 and 2. The enhanced-specificity anchor primers, $T_{12}GGA$ in lanes 3 and 4, $T_{12}GGC$ in lanes 5 and 6, $T_{12}GGG$ in lanes 7 and 8, and $T_{12}GGT$ in lanes 9 and 10 are shown. The comparisons showed that: (1) some, but not all, of the cDNAs generated by traditional anchor primers are also generated by the four derived enhanced-specificity anchor primers; (2) each enhanced-specificity anchor primer displays a number of cDNA species that remain undetected with the traditional parent anchor primer, and which are uniquely its own; and (3) the behavior of these enhanced-specificity anchor primers, with respect to optimum cDNA input and cycling parameters, parallels that of their parent anchor primers.

The enhanced-specificity anchor primers were also found in rescue failed reactions produced by the traditional anchor primers and this is shown in FIG. 6. In FIG. 6 the first lane of each group shows the failed differential display reaction; the additional lanes show the rescue of the reaction by the enhanced-specificity anchor primers. Lane M in all groups is the molecular weight marker. Group 1 consists of the parent anchor primer in lane 1, $T_{12}AA$; and the enhanced-specificity anchor primers in lane 2, $T_{12}AAA$; lane 3; $T_{12}AAC$; lane 4, $T_{12}AAG$; and lane 5, $T_{12}AAT$. Group 2 consists of the parent anchor primer in lane 6, $T_{12}AT$; and the enhanced-specificity anchor primers in lane 7, $T_{12}ATA$; lane 8, $T_{12}ATC$; lane 9, $T_{12}ATG$; and lane 10, $T_{12}ATT$. Group 3 consists of the parent anchor primer in lane 11, $T_{12}CT$; and the enhanced-specificity anchor primers in lane 12, $T_{12}CTA$; lane 13, $T_{12}CTC$; lane 14 $T_{12}CTG$; and lane 15, $T_{12}CTT$. Group 4 consists of the parent anchor primer in lane 16, $T_{12}GT$; and the enhanced-specificity anchor primers in lane 17, $T_{12}GTA$; lane 18, $T_{12}GTC$; lane 19, $T_{12}GTG$; and lane 20, $T_{12}GTT$. In the first lane of each group (e.g. lanes 1, 6, 11 and 16), the PCR amplification fails to yield discrete cDNAs. In the subsequent lanes of each group, the enhanced-specificity anchor primers rescue most of the reactions (except lanes 10, 15 and 20). The employment of the enhanced-specificity anchor primers greatly improved the robustness of the differential display technique.

Of course, other primers in addition to the 3' anchor primer may be used if desired, such as an arbitrary upstream, or 5', primer, which can be a decamer primer or another primer known to those of ordinary skill in the art.

Figure 7A:
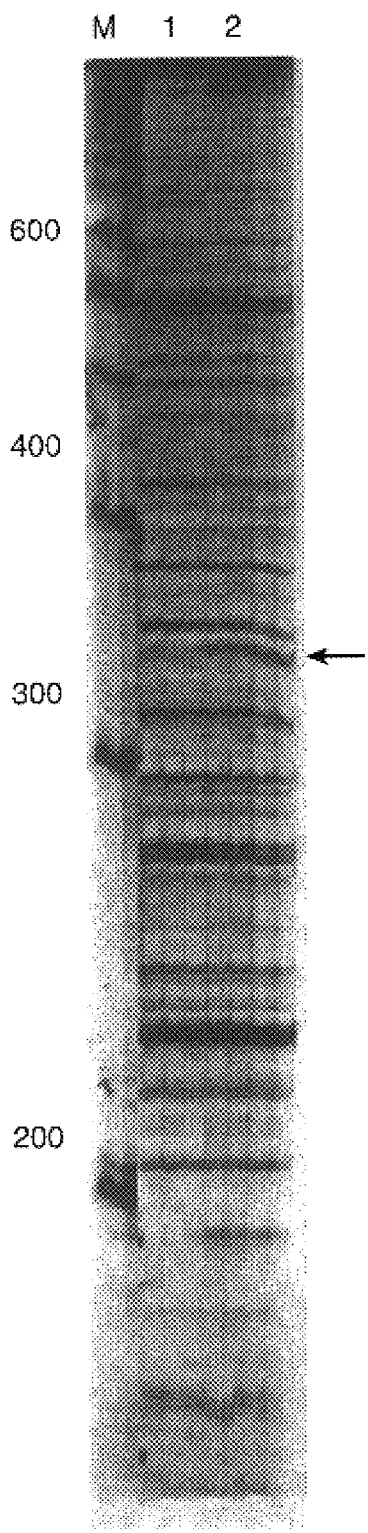
FIGS. 7A–C are photographs of gels demonstrating the problems associated with the presence of contaminating cDNAs within the gel of interest.
Figure 7B:
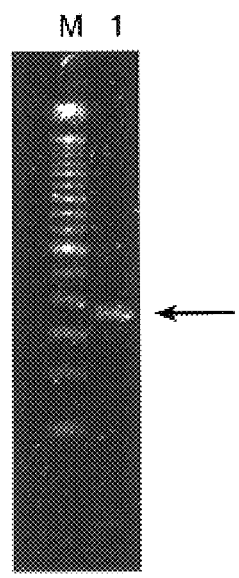

Referring again to FIG. 1, after the PCR step, a subtraction step is preferably performed. This subtraction step is expected to reduce the cloning of non-specific cDNAs that contaminate the cDNA of interest as visualized by the differential display gel. The problem that necessitates such a step is illustrated in FIG. 7. Lanes 1 and 2 (in triplicate) illustrate the comparison between the differential display pattern of two different mRNA samples. A differentially displayed cDNA is identified by the arrow in the lanes marked #2 shown in FIG. 7A. The cDNA is eluted from the gel and reamplified. The reamplified product appears to contain a single cDNA as shown in lane 1 of FIG. 7B.

Figure 7C:
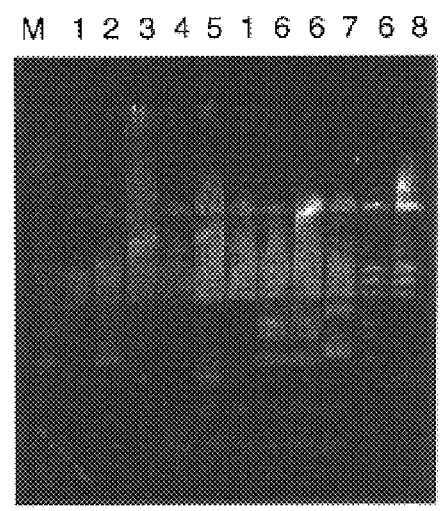

It was assumed previously that standard analyses with the use of restriction enzymes (such as EcoRI) would yield single cDNA species after cloning into the plasmid vector. However, after subcloning and fingerprinting with restriction enzyme Hinf I, it was found that eight differential products have been subcloned as illustrated in FIG. 7C. Lane M in all panels is the molecular weight marker. If the contaminating cDNAs could be removed before the subcloning step, then the labor intensive step of sorting through subclones until the correct one is identified could be avoided.

The subtraction step of the method of this invention substantially eliminates the contaminating products by hybridizing them with products derived from the corresponding negative location. The hybrids can then be removed and the remaining cDNA can be re-amplified. Furthermore, it is not inconceivable that the subtraction step could also enrich for differentially expressed cDNAs which are not visible by eye on the differential display gel.

Figure 8:
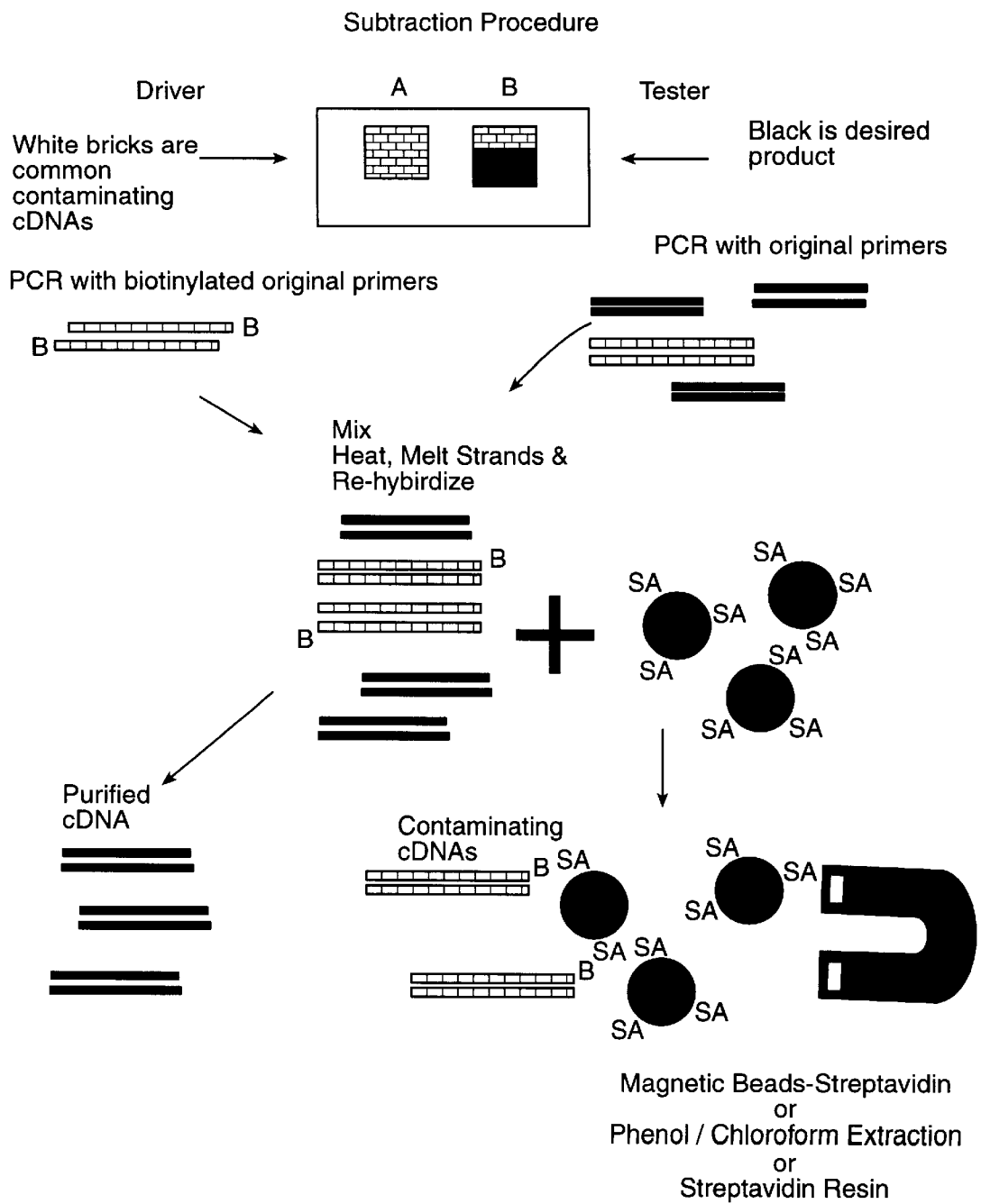
FIG. 8 depicts the method of using subtraction to eliminate substantially the presence of contaminating cDNA.

The subtraction procedure of this invention is generally outlined in FIG. 8. The product that is differentially expressed is cut out of the gel and amplified with the original primers. This is called the "tester cDNA" and contains both the desired and contaminating cDNAs. The corresponding negative location contains mostly contaminating cDNAs. This spot is cut out of the gel and the products are amplified with the primers previously utilized in the method of this invention and in the presence of biotinylated deoxynucleotide substrates available from suppliers such as GIBCO BRL (Gaithersburg, Md.). Preferably, the original primers are biotinylated at the 5' end as available from such suppliers as Genosys (The Woodlands, Tex.). The amplified cDNA is called the "driver cDNA". The driver cDNA is labeled with biotin after it is eluted form the gel. The tester cDNA is not labeled. The tester cDNA is mixed with an excess of driver cDNA and heated to between about 90 and 100° C. for from about ten to about fifteen minutes to melt the double-stranded DNA molecules. The solution is kept at from about 55 to about 65° C. for from about 24 to about 48 hours and then allowed to come to room temperature (e.g., from about 20 to about 25° C.), allowing complementary strands of DNA to hybridize. Since the biotinylated driver cDNA is in great excess, it will find and hybridize to the contaminating cDNAs in the tester sample. The cDNA hybrids that contain biotin are then preferably removed from the solution by extraction with phenol/chloroform, by passing through a resin that contains streptavidin or by magnetizable beads that have been coated with streptavidin (FIG. 8), or another means known to those of skill in the art. Streptavidin, for example, binds biotin very tightly. The magnetizable beads are then isolated with a magnet and carry along the contaminating cDNAs that are common to both the tester and driver populations. The remaining purified cDNA product from the tester population is re-amplified and cloned into a plasmid vector.

Figure 9A:
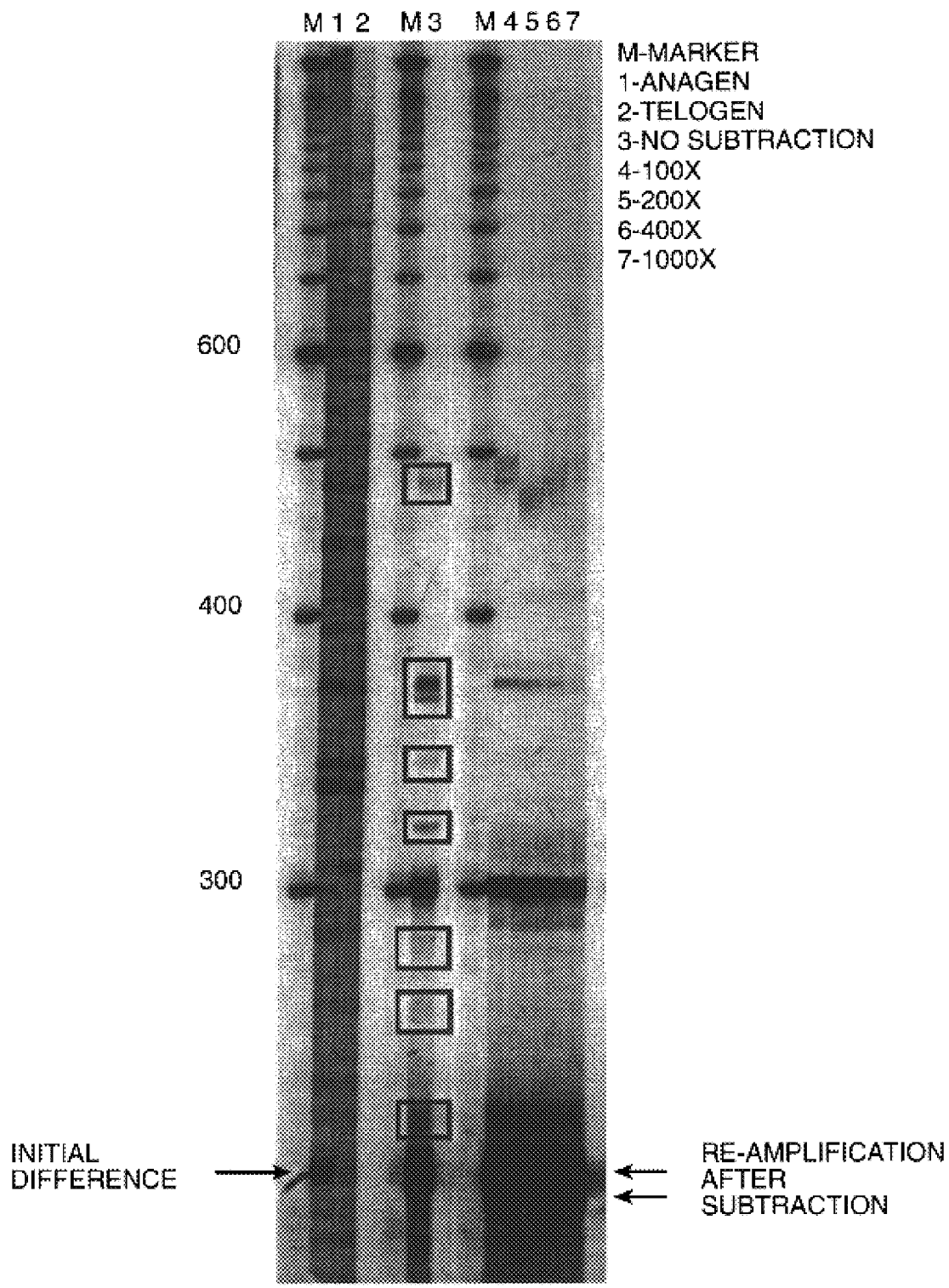
FIGS. 9A–9C is a photograph of gels demonstrating the reduction of contaminating cDNAs through the use of the subtraction procedure without the use of biotinylated primers.
Figure 9B:
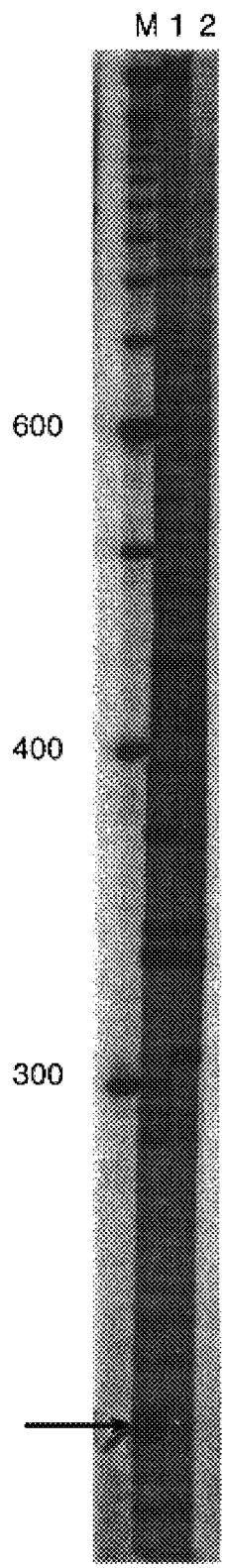
Figure 9C:
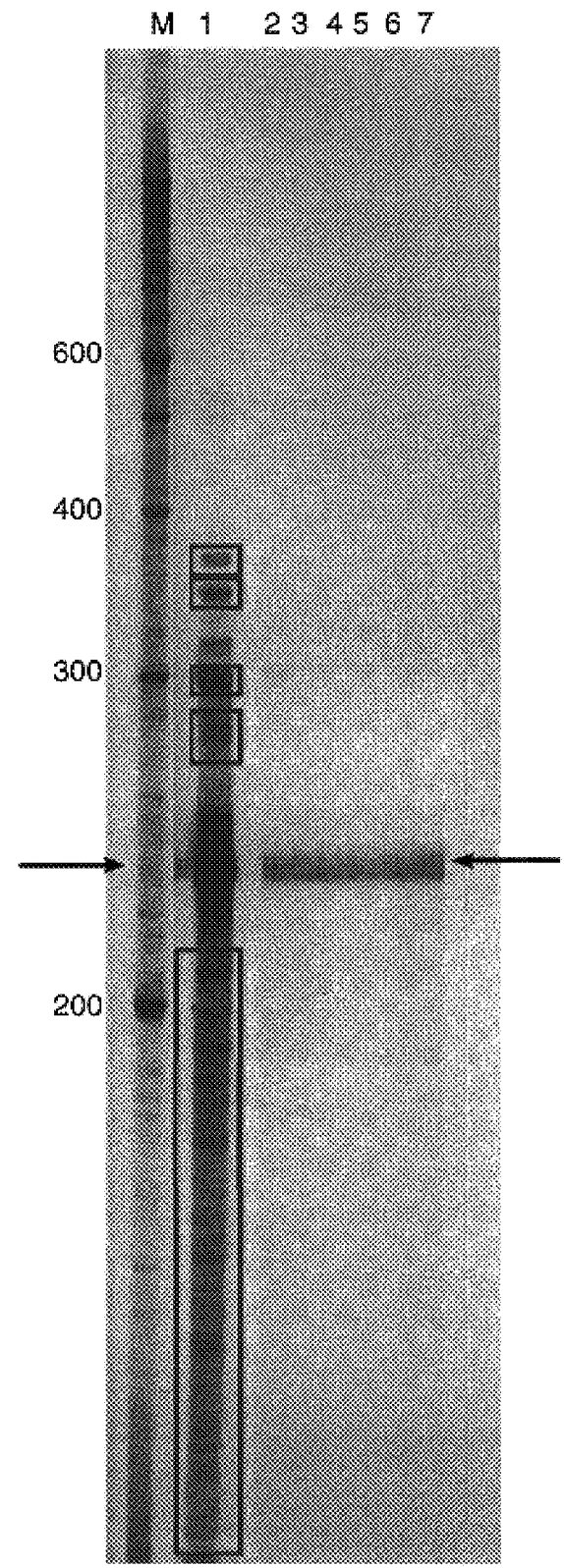

The efficiency of the subtraction procedure is demonstrated in FIG. 9A. Lanes 1 and 2 compare the differential display patterns of two different mRNA samples. A differentially displayed cDNA is identified in lane 1. After isolation, this cDNA and several other contaminating cDNAs have also been re-amplified and are shown by the boxed cDNAs in lane 3. After the subtraction procedure, most of the contaminating cDNAs are removed as shown in lanes 4–7 of FIG. 9A. A more refined result of this method is shown in FIGS. 9B and 9C. In FIG. 9B, the same initial difference is depicted between lanes 1 and 2. After elution and re-amplification, multiple contaminates are again seen in lane 1 of FIG. 9C. The boxed cDNA in lane 1 are contaminants while the arrows point to the cDNA of interest. After subtraction, only a single cDNA species remains in lanes 2–7. Lane M in all panels is the molecular weight marker. This procedure greatly facilitates the cloning of the cDNA of interest.

The following examples demonstrate the mechanism and utility of this invention. They do not serve to limit the scope of the invention, but merely to illustrate the ways in which the method and compositions of this invention may be performed.

EXAMPLE 1

Preparation of RNA

RNA may be produced using the following procedure. Total RNA from mouse dorsal skin was isolated by a modification of a single-step procedure (Chomczynski and Sacchi, 1987). Briefly, dorsal skin frozen in liquid nitrogen was ground up in a mortar and immediately homogenized using a Brinkman Polytron (PT 3000) for 60 seconds at 30,000 rpm in RNA STAT-60™ as recommended by the vendor (TEL-TEST "B", Inc., Friendswood, Tex.). After addition of 0.2 volume of chloroform per volume of RNA STAT-60™ and centrifugation (12,000 g for 10 minutes at 4° C.), the RNA in the aqueous phase was precipitated with isopropanol (0.5 ml per ml of homogenate) and collected by centrifugation (12,000 g for 10 minutes at 4° C.). The RNA pellet was digested with 100 $\mu$g/ml proteinase K (Boehringer Mannheim Biochemica) in 10 mM Tris-HCl (pH 7.5), 0.1 mM EDTA, 0.1% sodium dodecyl sulfate at 37° C. for 30–60 minutes. The solution was made 0.3 M in NaOAc (pH 5.2), and the RNA was purified by extraction with phenol:chloroform:isoamyl alcohol [25:24:1 (v/v/v)] and precipitated with 2.5 volumes of ethanol. Poly(A)$^+$ mRNA was isolated by two cycles of chromatography on oligo(dT)-cellulose using a standard protocol (Ausubel et al., 1987). Twice-selected poly(A)$^+$ mRNA was precipitated by adjusting the salt concentration to 0.3 M NaOAc (pH 5.2), and adding 2.5 volumes of ethanol. The precipitated RNA was collected by centrifugation (12,000 g for 1 hour at 4° C.) in a Beckman SW-41 rotor. The pellet was washed with 70% ethanol, recentrifuged, allowed to air dry lightly and resuspended in diethylpyrocarbonate-treated water (DEPC).

EXAMPLE 2

Synthesis of Single-Stranded cDNA

Poly(A)$^+$ mRNA produced in Example 1 was reverse transcribed using reagents and a modified protocol from GIBCO BRL (cDNA Synthesis System, Cat. No. 8267SA). In brief, 5 µg of poly(A)+ mRNA and 2.5 µg of oligo(dT)$_{12-18}$ primer (Promega) were combined in a 15 µl final volume. The solution was heated to 70° C. for 5 minutes, quenched on ice, and microfuged to collect solvent at the bottom. The following components were added sequentially to the annealed primer/template on ice: 4 µl (40 U/µl) RNasin ribonuclease inhibitor (Promega), 5 µl 0.1 M dithiotreitol, 10 µl 5× first strand buffer [250 mM Tris-HCl (pH 8.3),375 mM KCl, 15 mM MgCl$_2$], 2.5 µl of 10 mM each deoxynucleotide mix (dATP, dCTP, dGTP, dTTP), 11 µl DEPC-treated water, and 2.5 µl Moloney-murine leukemia virus (M-MLV) reverse transcriptase. The tube was vortexed gently to mix the reactants, and a tracer reaction was set up (to assess the size range of cDNA products on alkaline agarose gel) by transferring 5 µl of the mixture to a second tube containing 0.5 µCi of dried [$\alpha^{32}$P]dATP (3000 Ci/mmol from Amersham). Both reactions were incubated at 37° C. for 1 hour, at the end of which the tubes were microfuged and placed on ice. The main (non-radioactive) reaction was stopped by adding 2 µl of 0.5 M EDTA and 2 µl 10% SDS. Template RNA was digested with 6 µl 0.3 N NaOH and incubation at 65° C. for 1 hour. The reaction was neutralized with 20 µl 1 M Tris-HCl (pH 7.4), and 6 µl 2 N HCl. The solution was extracted once with phenol:chloroform:isoamy alcohol [25:24:1 (v/v/v)] followed by one extraction with chloroform:isoamyl alcohol [24:1 (v/v)]. The cDNA was precipitated with 0.5 volume of 7.5 M NH$_4$OAc and 3 volumes of ethanol (cooled to −20° C.), and was collected by immediate centrifugation at room temperature for 15 minutes. The pellet was washed once with 0.5 ml 70% alcohol (cooled to −20° C.), recentrifuged and dried lightly in air. The pellet was resuspended in 100 µl of 10 mM Tris-HCl (pH 7.4), 0.1 mM EDTA (TLE). Contaminating oligo(dT) primer was removed by chromatography on a spin column of Sephadex G-50 (Boehringer Mannheim Biochemica) equilibrated with TLE. The concentration of the cDNA was carefully determined by its measured absorbance at 260 nm.

EXAMPLE 3 cDNA Amplification and Electrophoretic Analysis

One-primer and two-primer PCR amplifications were carried out in duplicate in a total volume of 20 µl using the cDNA produced in example 2. The effects of various reaction components and cycling parameters on the robustness, reliability and size of amplified products have been examined. Preferably, proof-reading Taq polymerases in fairly basic reaction buffer such as that provided by the TaKaRa Shuzo Co. (distributed by PanVera Corporation, Madison, Wis.) should be used, as they result in the sharpest displays and the consistent generation of the largest cDNA products (>1.6 kilobases or kb). ExTaq (with ExTaq buffer), available from the TaKaRa Shuzo Co., is most preferred. Furthermore, deoxynucleotide concentration has a large effect upon the size of the amplified cDNAs. Preferably, the reaction dNTP concentration should be about 30 µM. Below this dNTP concentration, amplification of large cDNAs (>1 kb) falls off gradually, while at higher concentrations, the intensity of bands corresponding to smaller cDNAs (<500 base pairs or bp) becomes progressively weaker. The time allocated to primer annealing during PCR affects the overall intensity of the resulting display. An annealing time of about two minutes is most preferred. Annealing temperatures of from about 35° C. to about 45° C. is preferable, although temperatures above about 42° C. cause some results to become somewhat erratic. PCR extension time has the most direct influence on the size of amplified cDNAs. An extension time of about 30 seconds is preferred, although longer extension times favor even larger products. However, an increase in extension time should be accompanied by a reduction in the amount of cDNA input for PCR. Otherwise, the reaction generates high molecular weight products which cannot be resolved by PAGE.

Primers used were obtained as follows. Upstream deoxyoligonucleotide decamer primers of arbitrary sequence were purchased from Genosys Biotechnologies, Inc. (The Woodlands, Tex.). These primers are designed to be 50% in G+C content, and to be devoid of complementary ends as well as of the ability to generate hairpin structures. Anchor primers (T$_{12}$MN) were also purchased from Genosys and are as originally described (FIG. 4A, Liang and Pardee, 1992). Enhanced-specificity anchor primers T$_{12}$MNN (where M can be A, C or G and N can be A, C, G or T) were designed by incorporation of an additional deoxynucleotide to the 3' end of the original anchor primers (FIG. 4B). This modification generates four distinct enhanced-specificity anchor primers from each of the traditional anchor primers (e.g. from T$_{12}$AA, are derived the following enhanced-specificity anchor primers: T$_{12}$AAA, T$_{12}$AAC, T$_{12}$AAG, T$_{12}$AAT).

The reactions were set up by mixing on ice 10 µl of the appropriate cDNA solution together with 10 µl of PCR master mix. Preferably, the final reaction mixture should contain from about 0.1 to about 10 µM 3' anchor primer, from about 0.1 to about 10 µM 5' arbitrary decamer, from about 10 to about 50 µM dNTPs, from about 0.1 to about 5 µCi [$\alpha^{33}$P]dATP (3000 Ci/mmol, Amersham), about 0.4 µl of ExTaq polymerase (5 U/µl) (TaKaRa Shuzo Co., LTD.), about 2 µl 10× ExTaq PCR buffer (TaKaRa Shuzo Co., LTD.), and about 4.4 µl DEPC-treated water. These proportions can be adjusted, but always must add up to 10 µl. For single primer PCR reactions, the final primer concentrations should be from about 2 to about 10 µM for 3' anchor (or enhanced-specificity anchor primer), and from about 2 to about 10 µM for 5' arbitrary decimer. In this example, 2.5 µM of 3' anchor primer, 0.5 µM arbitrary decamer, 30 µM of DNTP, 2 µCi [$\alpha^{33}$P]dATP (3000 Ci/mmol, Amersham) were used. In the PCR reactions, 2.5 µM for 3' anchor and 4 µM of 5' arbitrary decamer were used.

Reactions were layered with mineral oil and centrifuged briefly. PCR should be carried out using a thermocycler programmed for from about 30 to 50 cycles, about 92 to 99° C./30–60 s, 35–45° C./30–120 s, 65–75° C./15–60 s. In this example, the thermocycler was programmed for 40 cycles of 94° C./30 seconds, 42° C./2 minutes and 72° C./30 seconds, with a final extension of five minutes at 72° C. An equal volume (20 µl) of formamide sequencing dye (95% formamide, 0.01% bromophenol blue, 0.01% xylene cyanol) was added to the completed reactions. The products were denatured at 90–100° C. for 5 minutes. The denatured samples (6 µl) were size-fractionated on 6% polyarylamide denaturating (7–8 M urea) sequencing gels. The gels were fixed for 10–45 min (5% methanol/5% acetic acid), transferred onto Whatman paper, dried for 0.5 to 3 h at 80° C., and autoradiographed.

EXAMPLE 4

Recovery of Differentially Displayed cDNAs

Reactions that generated detectable differences in the step set forth in Example 3 were re-run (when necessary) in order to achieve maximum separation of differentially displayed products from contaminating neighboring cDNAs. The X-Ray film and gel were aligned with each other by means of radioactive ink dots placed asymmetrically on the piece of Whatman paper onto which the gel had been dried. The film was lined up over the dried gel and sectors of the latter (corresponding to differentially expressed cDNAs) were excised using as template the windows that had been cut previously in the film. Gel slices (along with their paper backings) were soaked (10) 5–30 minutes in (1 ml) 0.25–1.5 ml 10 mM Tris pH 7.4/1 mM EDTA (TE) in order to remove urea. The gel slices were transferred to siliconized tubes containing (100) 25–150 µl STE (10 mM Tris-HCl (pH 8), 1 mM EDTA, 100 mM NaCl). The tubes were placed in boiling water for (10) 5–15 minutes, and incubated overnight at room temperature. The supernatants were transferred to fresh siliconized tubes. The samples were desalted by eluting with water after purification using the QIAquick PCR Purification Kit (QIAGEN, Chatsworth, Calif.). The samples were dried in vacuum, the cDNA residue was resuspended in (10) 5–15 µl of water and the entire sample was reamplified, after adding (10) 5–15 µl of master mix, precisely as described above.

EXAMPLE 5

Subtraction of Contaminating cDNAs

Sectors of the dried gel produced in Example 4 corresponding to both the (+) or "tester", and (−) or "driver" position of differentially displayed species were excised, and their cDNA contents were eluted and reamplified by PCR in separate 40 µl-reactions as already described. The driver cDNA was re-amplified in the presence of biotin-dCTP:dCTP and most preferably biotin-dATP:dATP. The incorporation of biotin-dGTP:dGTP and biotin-dTTP:dTTP may also work as well. The molar ratio of biotinylated-deoxynucleotide to deoxynucleotide may range from 1:7 to 7:1, preferably from 3:7 to 5:1 and most preferably from 9:11 to 13:5. The most preferred amplification employed both biotinylated primers in the reaction and a biotinylated deoxynucleotide substrate to generate the driver material. The (−) position re-amplified material was preferably carried through a second round and most preferably a third round of amplification. The thrice-reamplified biotinylated material constitutes the "driver" for the subsequent subtractions. The preferred re-amplified materials were simultaneously desalted, resuspended in water, and unincorporated dNTPs were removed using Ultrafree-MC Centrifugal Filter units (Millipore Bedford, Mass.) or another similar method known to those of ordinary skill in the art. The concentration of the materials was determined by spectrophotometry. One microliter of "tester" cDNA was combined (in separate siliconized 0.65 ml tubes) with 100, 200, 400 and 1000-fold excess (by weight) of biotinylated "driver" cDNA. Higher excess amounts of biotinylated "driver" cDNAs can be used in the subtraction step. The combined materials were vacuum-dried and resuspended in 2.5–10 µl of hybridization buffer without salt (HB-NaCl, HEPES 50 mM pH 7.6, SDS 0.2%, EDTA 2 mM). The solution was overlaid with mineral oil and heated at 90–100° C. for 5–15 minutes. The sample was quenched in ice-water and 0.5–1.5 µl of 0.5 M NaCl was introduced through the oil. The solution was incubated at 55–75° C. for 24–36 hours. The sample was diluted with 50–150 µl of hybridization buffer without SDS (HB-SDS, HEPES 50 mM pH 7.6, EDTA 2 mM, NaCl 500 mM), 5–30 µg streptavidin were added and the mixture was incubated at room temperature for 1–10 minutes. The reaction was extracted with 10 mM Tris 1 mM EDTA saturated phenol:chloroform (1:1). The aqueous phase was removed, and the organic phase was washed with 15–50 µl HB-SDS. The streptavidin and phenol:chloroform treatment was repeated twice more on the pooled aqueous phase. The solution was concentrated and desalted by means of the Millipore filtering units as already described. The remaining solution was vacuum-dried, resuspended in 5–30 µl of water and reamplified by PCR as already described. The product generated is the essentially pure differentially displayed cDNA species.

EXAMPLE 6

Cloning and Sequencing of Differentially Displayed cDNAs

The ends of the purified, reamplified cDNAs produced in Example 5 were made flush prior to blunt-end ligation according to a standard protocol (Sambrook et al., 1989). Blunt-end cDNAs were separated from primers, nucleotides, polymerases, and salts using methods or kits known in the art such as the QIAquick PCR Purification Kit (Qiagen Inc., Santa Clarita, Calif.). The cloning vector was digested with the restriction enzyme Sma I, gel purified and dephosphorylated following a standard protocol (Sambrook et al., 1989). The cDNAs were cloned by blunt-end ligation using a protocol provided by the supplier of the cloning vector [pBluescript II SK(+) Exo/Mung DNA Sequencing System, Stratagene, La Jolla, Calif.]. The ligation products were used to transform MAX Efficiency DH5a™ Competent Cells according to a protocol provided by the supplier (GIBCO BRL, Gaithersburg, Md.). Positive clones were identified by blue-white selection. White colonies were analyzed for the presence and size of cDNA inserts via agarose gel electrophoresis following PCR amplification of the cDNAs using the T3 and T7 RNA polymerase priming sites flanking the polylinker of the cloning vector. The potential presence of several different, yet identically-sized, cDNAs in the cloned population was assessed by agarose gel electrophoresis following digestion of up to 20 similarly-sized PCR-amplified inserts (derived from different bacterial transformants) using one or more restriction enzymes having tetranucleotide recognition sequences such as Hinf I, Rsa I, HhaI, as set forth in FIG. 7C. Probes were prepared from all distinct cDNAs having the correct anticipated size, and the level of expression of their cognate RNAs were assessed by Northern analysis. Double-stranded DNA sequencing was carried out by methods known in the art such as the dideoxynucleotide chain-termination method using the Sequenase Version 2.0 Kit (United States Biochemical, Cleveland, Ohio) and flanking, oppositely-oriented T3 and T7 promoter primers (New England BioLabs, Beverly, Mass).

EXAMPLE 7

Northern Blot Analysis

Northern blot analysis was carried out according to standard conditions (Sambrook et al., 1989) on the original mRNA samples isolated in Example 1 in order to compare the expression levels of the newly identified cDNA from Example 6. Essentially, 10 µg of total RNA, or 1 µg of poly(A)+ mRNA were electrophoresed in 1% agarose-0.66 M formaldehyde gels and then transferred onto nylon membranes. Following transfer, filters were UV-crosslinked and baked at 80° C. for 1 hour. Filters were either used immediately or stored at 4° C. in heat-sealable plastic bags. Hybridization was carried out using random-primed [γ32P] ATP labeled cDNA probe in 50% formamide at 45° C. for 18 hours using standard conditions. Filters were washed with shaking for 0.3 hour at room temperature in 2×SSC (sodium chloride 300 mM and sodium citrate 30 mm pH 7.0)/0.1% SDS, followed by two 15 minute washes at 45° C. in 0.1×SSC/0.1% SDS. For rehybridization, probes were removed from the filters by soaking for 0.45 hour with gentle agitation at 90° C. in 0.5×Denhardt's solution (Sambrook et al., 1989), 25 mM Tris-HCl (pH 7.5), 0.1% SDS, followed by a 15 minute wash in deionized water prewarmed to 65° C.

EXAMPLE 8

Figures 10A, 10B:
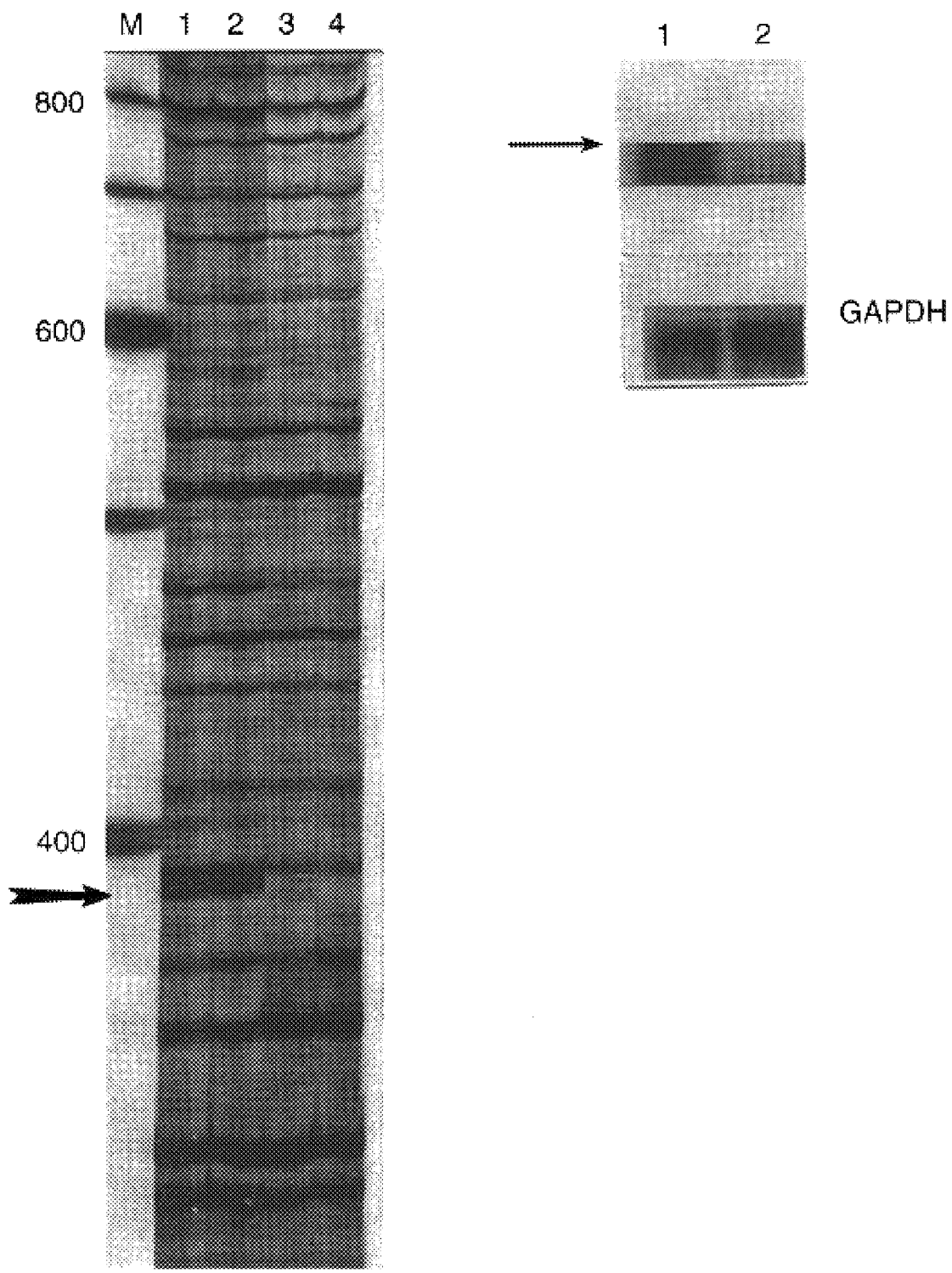
FIG. 10A is a photograph of a gel showing the identification of a differentially displayed cDNA.
FIG. 10B is a photograph of a membrane showing Northern verification.
Figure 10C:
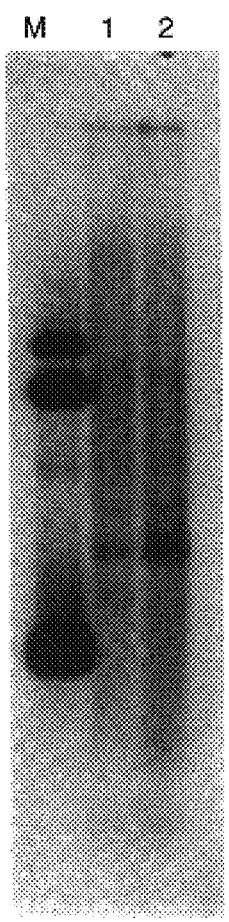
FIGS. 10C, 10D and 10E are additional examples of Northern analysis verifying identified differences between anagen and telogen mRNA's.
Figure 10D:
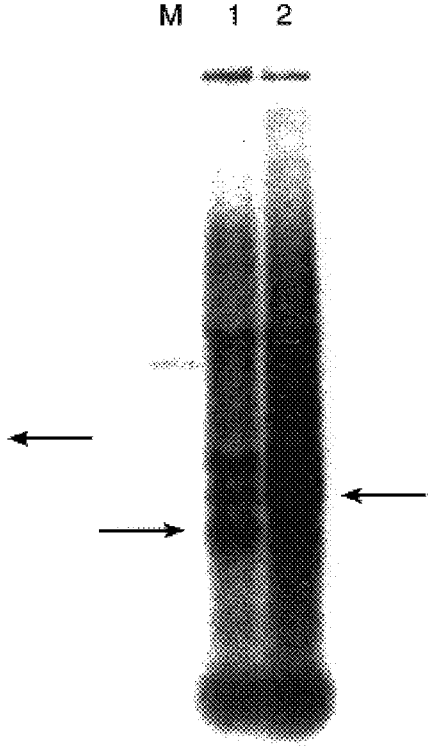
Figure 10E:
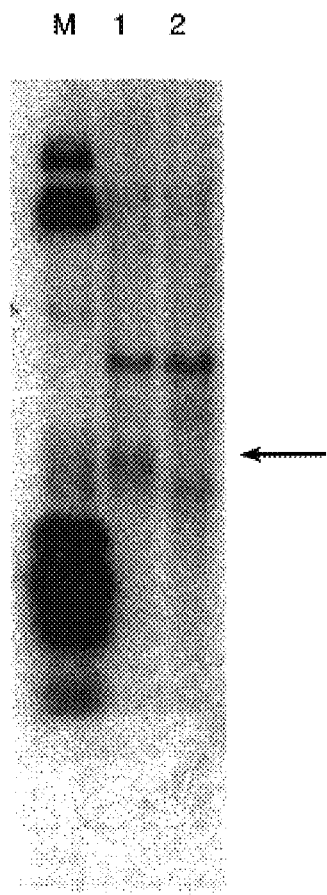

Application of Differential Display to the Isolation of Genes Regulating Hair Growth The hair follicle is a dynamic structure which undergoes elaborate cycles of growth, (anagen), rest (telogen), and regression (catagen). However, the molecular basis for the initiation of hair growth, as well as the controls of the various phases of the hair cycle, remain largely unelucidated. The differential display method of this invention was used to isolate genes which may play a role in the initiation of anagen in the adult mouse hair follicle. A randomly selected differentially displayed cDNA and its verification by Northern analysis demonstrates the power of the revised technique (FIG. 10). In FIG. 10A, the molecular weight marker is in lane M. The PCR products generated using anchor primer $T_{12}GG$ using mRNA populations derived from anagen and telogen mouse skin were compared by single-primer Differential display and are shown in duplicate reactions in lanes 1–2 (anagen) and lanes 3–4 ) telogen respectively. The arrow indicates a cDNA species that is up-regulated in anagen. FIG. 10B shows the Northern verification of differentially displayed cDNA. The membrane contains anagen and telogen cDNAs in lanes 1 and 2 respectively and was probed with the cDNA that was differentially displayed and isolated (top panel). The bottom plane shows the same membrane that was stripped and hybridized with a probe for the housekeeping gene glyceraldehyde-phospho-dehydrogenase (GAPDH) to demonstrate the loading of equal amounts of RNA in each lane. FIGS. 10C, 10D and 10E depict three more examples of Northern analysis of cDNAs intiially amplified with the T12GGA primer and isolated through the subtraction procedure. In FIGS. 10C, 10D and 10E lane M is the molecular weight marker, lane 1 is mRNA from anagen and lane 2 is mRNA from telogen. Arrows denote differentially displayed messages.

The following abbreviations and definitions have been used herein and are provided for the guidance and information of the reader:

| | |
|---|---|
| A | Adenine |
| Anchor primer | A special primer that binds to the poly A tail of the mRNA and cDNA |
| Arbitrary Upstream Decamer | A special primer that binds arbitrarily within the mRNA and cDNA |
| C | Cytosine |
| cDNA | complementary DNA |
| DNA | Deoxynucleic acid |
| dNTP | deoxynucleotide triphosphate |
| Downstream Primer | The primer that binds downstream during PCR |
| G | Guanine |
| mRNA | messenger RNA |
| PCR | polymerase chain reaction |
| Primer | A small piece of DNA 10 to 20 nucleotides that is needed so the Taq Polymerase can catalyze |
| the PCR Reverse converts mRNA | Transcriptase, the enzyme that into cDNA |
| RNA | Ribonucleic acid |
| T | Thymidine |
| $T_{12}NNN$ | TTTTTTTTTTTTNNN |
| Taq Polymerase | The working enzyme in PCR |
| Upstream Primer during PCR | The primer that binds upstream |

Arbitrary Upstream Oligonucleotides (Decamers)

| | |
|---|---|
| D6 | 5'AAACTCCGTC3' |
| D7 | 5'TCGATACAGG3' |

---

What is claimed is:

1. A method of obtaining a purified DNA complementary to an mRNA that is differentially expressed in two nucleic acid samples comprising the steps of:

(a) providing a first nucleic acid sample including mRNA molecules;

(b) providing a second nucleic acid sample including mRNA molecules;

(c) contacting each of said first nucleic acid sample and said second nucleic acid sample with a first oligodeoxynucleotide primer that hybridizes to a first site in mRNAs in said first and second nucleic acid samples;

(d) reverse transcribing said mRNAs to which said first primer hybridizes to produce a first population of DNA strands that are complementary to said mRNAs in said first nucleic acid sample to which said first primer hybridizes, and a second population of DNA strands that are complementary to said mRNAs in said second nucleic acid sample to which said first primer hybridizes;

(e) quantifying the amount of complementary DNA strands produced as a result of the reverse transcription step;

(f) titrating said complementary DNA strands by running at least two different concentrations of the complementary DNA through a polymerase chain reactor and simultaneously contacting said first and second populations of DNA strands with a second oligodeoxynucleotide primer that hybridizes to a second site in said first and second populations of DNA strands, which second primer comprising $T_{12}MNN$, wherein M is A, G or C and N is A, G, C or T, said contacting being performed under conditions in which said second primer hybridizes with at least some of the DNA strands in said first and second populations;

(g) amplifying portions of the DNA strands in said first and second populations of DNA strands with said second primer to produce a first and a second population of amplification products;

(h) comparing the presence or level of individual amplification products in said first and second populations of amplification products; and (i) subtracting contaminating cDNAs from the amplification products, thereby resulting in a purified DNA complementary to mRNA that is differentially expressed in the samples.

2. A method according to claim 1 wherein said first oligodeoxynucleotide primer comprises an oligo dT primer having from about 12 to about 18 thymidine nucleotides.

3. A method according to claim 1 wherein step (i) comprises selecting a driver cDNA and a tester cDNA sample, contacting said driver cDNA with a first oligonucleotide primer, amplifying said driver cDNA in the presence of a biotinylated oligonucleotide substrate, contacting said tester cDNA with a second oligonucleotide primer, amplifying said test cDNA in the presence of a oligonucleotide substrate, reacting said driver cDNA sample in excess with said tester cDNA sample, heating said mixture and allowing said mixture to cool such that undesirable cDNA is hybridized with a biotinylated deoxynucleotide, and removing said biotinylated cDNA hybrids from the reaction.

4. A method according to claim 3 wherein said biotinylated deoxynucleotride substrate comprises biotinylated deoxynuleotide and non-biotinylated deoxynucleotide, said composition having a molar ratio of biotinylated deoxynucleotide to non-biotinylated deoxynucleotide from about 1:7 to about 7:1.

5. A method according to claim 4 wherein said composition has a molar ratio of biotinylated deoxynucleotide to non-biotinylated deoxynucleotide from about 3:7 to about 5:1.

6. A method according to claim 4 wherein said composition has a molar ratio of biotinylated deoxynucleotide to non-biotinylated deoxynucleotide from about 9:11 to about 13:5.

7. A method according to claim 3 wherein step (g) further comprises the use of primers which are biotinylated at the 5' end in combination with a biotinylated deoxynucleotide substrate.

8. A method according to claim 3 wherein said biotinylated deoxynucleotide is selected from the group consisting of biotinylated adenine and biotinylated cytosine.

9. A method according to claim 8 wherein said biotinylated deoxynucleotide is biotinylated adenine.

10. A method according to claim 3 comprises wherein the step of removing said biotinylated cDNA hybrids from the reaction comprises passing said reaction mixture through streptavidin-containing resins.

11. A method according to claim 10 which further comprises removing said biotin-containing cDNA hybrids by adding magnetizable beads coated with streptavidin to the reaction mixture and isolating said beads with a magnet.

12. A method according to claim 3 which further comprises removing said biotin-containing cDNA hybrids by phenol:chloroform extraction after incubation with streptavidin.

13. A method of comparing the presence or level of individual mRNA molecules in two nucleic acid samples comprising the steps of:

(a) providing a first nucleic acid sample including mRNA molecules;

(b) providing a second nucleic acid sample including mRNA molecules;

(c) contacting each of said first nucleic acid sample and said second nucleic acid sample with a first oligodeoxynucleotide primer that hybridizes to a first site in mRNAs in said first and second nucleic acid samples;

(d) reverse transcribing said mRNAs to which said first primer hybridizes to produce a first population of DNA strands that are complementary to said mRNAs in said first nucleic acid sample to which said first primer hybridizes, and a second population of DNA strands that are complementary to said mRNAs in said second nucleic acid sample to which said first primer hybridizes;

(e) quantifying the amount of complementary DNA strands produced as a result of the reverse transcription step;

(f) titrating said complementary DNA strands by running at least two different concentrations of the complementary DNA through a polymerase chain reactor and simultaneously contacting said first and second populations of DNA strands with a second oligodeoxynucleotide primer that hybridizes to a second site in said first and second populations of DNA strands, which second primer comprising $T_{12}MNN$, wherein M is A, G or C and N is A, G, C or T, said contacting being performed under conditions in which said second primer hybridizes with at least some of the DNA strands in said first and second populations;

(g) amplifying portions of the DNA strands in said first and second populations of DNA strands with said second primer to produce a first and a second population of amplification products;

(h) comparing the presence or level of individual amplification products in said first and second populations of amplification products; and (i) subtracting contaminating cDNAs from the amplification products; and (j) comparing the presence or level of individual cDNA molecules in said first and second populations of amplification products that are complementary to mRNA molecules in said first and second populations of nucleic acid samples, and thereby determining the presence of complementary mRNA molecules in said first and second populations of nucleic acid samples.

\* \* \* \* \*